(12) United States Patent
Xu et al.

(10) Patent No.: US 6,531,505 B2
(45) Date of Patent: *Mar. 11, 2003

(54) IMMUNOSUPPRESSIVE AGENTS (75) Inventors: Qiang Xu, 5-1-602, 40 Ma Jia Jie, Nanjing City, Jiangsu Province, 210009, P.R. (CN); Ikuo Saiki, Fuchu-machi (JP); Ting Chen, Nanjing (CN); Katsuko Komatsu, Toyama (JP)

(73) Assignee: Qiang Xu, Nanjing (CN)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/393,704

(22) Filed: Sep. 10, 1999

(65) Prior Publication Data

US 2002/0040050 A1 Apr. 4, 2002

(30) Foreign Application Priority Data

Sep. 14, 1998 (JP) .......................................... 10-260412

(51) Int. Cl.$^7$ ................................................ A61K 31/35
(52) U.S. Cl. ....................................................... 514/456
(58) Field of Search ................................. 514/108, 456

(56) References Cited

U.S. PATENT DOCUMENTS 4,603,137 A * 7/1986 Bhat et al. .................. 424/769

* cited by examiner

Primary Examiner—Theodore J. Criares
(74) Attorney, Agent, or Firm—Crowell & Moring LLP (57) ABSTRACT An immunosuppressive agent which is very effective for treating autoimmune disease, inflammatory reaction, fibrosis or dysfunction caused by autoimmune disease and related disease thereof with tissue injury or infection, rejection of transplantation, graft versus host disease by bone marrow (hematopoietic stem cell) transplantation, or allergic disease, by selectively inhibiting the activated T cells, is provided.

7 Claims, 6 Drawing Sheets

IMMUNOSUPPRESSIVE AGENTS

BACKGROUND OF THE INVENTION

1. Field of the Invention

The present invention relates to an immunosuppressive agent, particularly to an immunosuppressive agent comprising a selective inhibitor of the activated T cells, as an active ingredient. More particularly, the present invention relates to a therapeutic agent for treating diseases due to abnormal immune response induced by the activated T cells, such as rejection for organ transplantation, graft versus host disease by bone marrow (hematopoietic stem cell) transplantation, autoimmune disease, inflammatory reaction, fibrosis or dysfunction caused by autoimmune disease or related disease thereof with tissue injury or infection, or allergic disease.

2. Description of the Prior Art

Immune system of an organism has been developed with surveillance and defense mechanism by recognition and elimination of pathogenic foreign microorganisms such as bacteria and viruses. Therefore, the organism distinguishes own cells or tissue (self-antigens) from foreign microorganism (nonself-antigens), and does not respond to the self-antigens, or respond to them having the failure to mount immune response (immunological tolerance). Accordingly, the organism has developed an acquired immunity to eliminate nonself-antigens immediately and efficiency.

In the immune system, T cells (T lymphocytes) play an important role. The naïve CD4T cells in the periphery are activated by receiving both the signal of antigen from antigen-presenting cells through a T cell receptor, and signals of other costimulatory molecules. Then, they proliferate secreting IL-2, i.e., T cell growth factor (Thp). The Thp differentiate to Th0 cells, then, separate to Th1 cells or Th2 cells. These cells further proliferate, produce a various kinds of cytokines and introduce a cytopathic effect.

When an abnormal reaction happens in this series of immune response, lymphocytes, especially T cells, strongly respond to self-antigens, and could generate a tissue injury. This state is called as autoimmune disease. One of the causes which trigger the abnormal immune response is that normal immune response against viruses or bacteria is changed to immune response against self-antigens by some kind of system. The tissue injury or infection induced by autoimmune disease, introduce a various kinds of inflammatory reaction, fibrosis of tissue or dysfunction, so on.

Although the rejection for organ transplantation or graft versus host disease by bone marrow (hematopoietic stem cell) transplantation is a normal immune response reaction, it is therapeutically desired to inhibit it. The mechanism of this immune response is basically the same, and the activated T cells play main role in the reaction.

Recently, the role of the activated T cells in allergic disease has drawn attention. Namely, it has been evidenced that cytokines such as IL-4 and IL-5 produced mainly by the activated Th2 cells, activate mast cells or eosinophile to induce immediate hypersensitivity, and interferon-γ (IFN-γ) produced mainly by Th1 cells induce delayed-type hypersensitivity.

Therefore, the therapeutic agent having selective inhibiting activity of the activated T cells for treatment of autoimmune disease, immunity of transplantation, chronic active-typed immunological inflammatory reaction caused by the disease mentioned before, and allergy disease has been desired.

Under these circumstances, therapeutic method to control the mediators in T cells activating mechanism has been studied. Among them, strong suppressive effect against T cells using cyclosporine or FK-506, anti-cytokine therapy, anti-adhesion molecule (activation related molecules) therapy, or monoclonal antibody has drawn attention. However, these compounds have not the potential selectivity against the activated T cells, similar to glucocorticoids used heretofore, and the problem of side effects still remains.

Incidentally, the autoimmune disease is systemic disease that may occur in any of organs. Furthermore, in accordance with the development of the organ transplantation and hematopoietic stem cell transplantation, the problem of rejection for transplantation and graft versus host disease is expected to increase. Additionally, allergic disease is called as "civilized disease", and there are great number of patients who are suffering from it, due to the difficulty of curing from the disease perfectly.

There are many diseases in which the activated T cells play main role, thus the development of the effective therapeutic agent for treatment thereof is desired. Nevertheless, there is no such an agent, at the present time, which selectively inhibit the activated T cells for the treatment of diseases cased by the activated T cells.

Accordingly, the object of the present invention is to provide an effective immunosuppressive agent having a selective inhibiting activity of the activated T cells, with low side effects. More particularly, the object of the present invention is to provide the therapeutic agent for treating autoimmune disease, inflammatory reaction occurred in autoimmune disease or related diseases thereof with tissue injury or infection, fibrosis, dysfunction, rejection for organ transplantation, graft versus host disease by bone marrow (hematpoietic stem cell) transplantation, and allergic disease.

SUMMARY OF THE INVENTION

In order to solve the problems, therefore, the present inventors have found out the compounds having selectively inhibiting activity of the activated T cells, by means of the mechanism of the selective induction of apoptosis in the activated T cells. Further, the present inventors have found out that these compounds have potential activities for preventing or controlling the diseases caused by activated T cells.

Accordingly, one aspect of the present invention is to provide the immunosuppressive agent comprising a selective inhibitor of the activated T cells, as active ingredient.

In the present invention, the activated T cells are those which proliferate by producing and secreting a various kinds of cytokines, then cause a series of the immune response.

Thus, the present invention is characterized by inhibition of the activated T cells by inducing selective apoptosis, and preventing or treating the diseases resulted from the abnormal immune response caused by these activated T cells.

Therefore, the specific aspect of the present immunosuppressive agent is to provide the agent for treating rejection for organ transplantation, graft versus host disease by bone marrow (hematopoietic stem cell) transplantation, autoimmune disease, inflammatory reaction caused by autoimmune disease or related disease thereof with tissue injury or infection, fibrosis, dysfunction or allergic disease.

The autoimmune diseases to be prevented and treated effectively by the immunosuppressive agent of the present invention are, for example, autoimmune hepatitis, rheuma- toid arthritis, insulin-dependent diabetes mellitus (IDDM), ulcerative colitis, multiple sclerosis (MS), scleroderma, myasthenia gravis, multiple myositis/dermatomyositis, Hashimoto's disease, autoimmune hypocytosis, Sjögren's syndrome, angitis syndrome or systemic lupus erythematosus, and so on.

In still another embodiment of the present invention, the allergic disease is, for example, bronchial asthma, allergic rhinitis, atopic dermatitis, urticaria, pollinosis, and so on.

The present immunosuppressive agent is therapeutically useful for preventing or treating the diseases by selectively inhibiting the activated T cells, with low side effects.

The compound, as the active ingredient of the present invention, can be selected by the measurement of apoptosis induction activity to the activated T cells for example, that isolated from mice with delayed-type hypersensitivity (DTH) reaction, as described later.

Based on the present inventor's investigation, they have found out the following flavanoids or chromones represented by the formula (I):

(I)

wherein,

R is hydrogen atom or a phenyl group which may be substituted with one or two hydroxy groups,

Rha is α-L-rhamnose residue, and dotted line indicates with or without double bond.

Accordingly, the another aspect of the present invention is to provide the immunosuppressive agent comprising flavanoids or chromones represented by the formula (I) as active ingredient.

Among them, chromones of formula (I), in which R is hydrogen atom, or flavanoides of formula (I), in which R is 4-hydroxyphenyl, 3,4-dihydroxypheny, or 3,5-dihydroxypheny are preferably used. More specifically, smitilbin of the formula (I-a), astilbin of the formula (I-b), engeletin of the formula (I-c) or eucryphin of the formula (I-d) is more preferable.

(I-a)

(I-b)

(I-c)

(I-d)

Some of the flavanoids or chromones of the present invention is known compound; however, their anti-inflammatory activities had been only examined, and their improvement activities of abnormal immune reaction have not been known. Smitilbin of the formula (I-a) is new compound discovered by the present inventors. Thus, still another embodiment of the present invention is to provide smitilbin of the formula (I-a) itself.

DETAILED DESCRIPTION OF THE INVENTION

The immunosuppressive agent of the present invention will be described in more detail using flavanoids or chromones of the formula (I) inducing apoptosis of activated T cells isolated from mice with delayed-type hypersensitivity (DTH) reaction.

The flavanoids or chromones of the formula (I), as an active ingredient of the present invention, is the compound from plant, for example, from *Smilax glabra Roxb.*, one of the plant of Liliaceae. The rhizome of *Smilax glabra Roxb.*, i.e., Rhizoma *smilacis Glabrae* is used for treatment of chronic dermatitis, syphilitic dermatitis, or mercury poisoning, as a domestic medicine in China.

The flavanoids or chromones of the formula (I), such as smitilbin (I-a), astilbin (I-b), engeletin (I-c) and eucryphin (I-d) may be obtained in pure form from Rhizoma *smilacis Glabrae* by extracting with suitable solvent, respectively.

The immunosuppressive agent of the present invention is not limited to the agent which contains pure form of the flavanoids or chromones as active ingredient. It can be the agent containing extract of plant such as Rhizoma *smilacis Glabrae* as an active ingredient comprising the flavanoids or chromones. The extract of Rhizoma *smilacis Glabrae* (hereinafter referred to as RSG ext) may be lyophilized powder form or liquid form.

The extraction may be performed by infiltration of plants with suitable solvents at room temperature or under refluxing. The dried and powdered plants are preferably used in this extraction process, and the solvent may be an organic solvent having medium polarity, lower alcohol, or water. For example, the solvent may be ethyl acetate, chloroform, petroleum ether, methanol, ethanol and water, and mixture thereof. The ratio of the solvent to the plants or dried powdered plants is not limited, and may vary in the range from about 5 to 10 times by weight of the plants with twice to fifth extraction proceeding. After extraction, the solvent was condensed to an appropriate amount, and the residue was purified by separate extraction using various kinds of solvents, chromatography, ion-exchange resin chromatography, or filtration by membrane to obtain the flavanoids or chromones of the present invention. Additionally, the synthetic flavanoids or chromones, or the extract obtained by any purified stages described above, may be used in the present invention.

The selective immunosuppressive activities against activated T cells possessed by the flavanoids or chromones of the present invention are confirmed by the apoptosis against activated T cells isolated from mice with delayed-type hypersensitivity (DTH) reaction. That is, the flavanoids or chromones of the present invention were cultured with the liver non-parenchymal cells (hereinafter, referred to as NPC) isolated from mice immunologicaly induced the liver injury with DTH reaction to give the cell death of non-adhesive fraction of NPC. In DNA fragmentation of gel agarose electrophoresis, DNA ladder' pattern had appeared, and the cell death was confirmed to be the apoptosis. The cell death by the flavanoids or chromones of the formula (I) was recognized in non-adhesive fraction (mainly composed by $CD4^+$ T cells and $CD8^+$ T cells), and not in adhesive fraction of NPC. Further, the cell death was not observed in hepatocytes cells (hereinafter, referred to as HC), NPC cells and spleen cells of normal mice. From these points, it is understood that the flavanoids or chromones of the formula (I) of the present invention are selectively inhibiting the T cells (mainly composed of non-adhesive fraction of NPC) activated by DTH reaction, and have effective selective immunosuppressive activity against that activated T cells.

Furthermore, the improvement effects on the injured tissue by selectively inhibiting the activated T cells, of the flavanoids or chromones of the formula (I) are also recognized by inhibiting the release of alanine aminotransferase (ALT) from HC isolated from mice with liver injury induced by DTH reaction.

Thus, the immunosuppressive agent of the present invention comprising the flavaoids or chromones of the formula (I), as active ingredient, induces selective apoptosis of the activated T cells, and consequently selectively inhibits these activated T cells. Therefore, the present immunosuppressive agent is useful for treating the diseases caused by the activated T cells, such as rejection for organ transplantation, graft versus host disease by bone marrow (hematopoietic stem cell) transplantation, autoimmune disease, inflammatory reaction caused by autoimmune disease or related disease thereof with tissue injury or infection, fibrosis, dysfunction or allergic disease.

The dosage forms of the present immunosuppressive agent containing the flavanoids or chromones of the formula (I), or the plant extract containing thereof, are not particularly limited. The flavanoids or chromones of the formula (I) can be prepared into various types of oral formulations or parenteral administration, including capsules, tablets, injection solutions using the conventional excipients.

For example, the flavanoids or chromones of the formula (I), or powdered extract is mixed with a suitable excipient such as lactose, starches or derivatives thereof or cellulose derivatives, and then filled in gelatin capsules.

Also, the tablets can be prepared by mixing the active ingredients with the above-mentioned excipients and further with binders such as sodium carboxymethylcellulose, alginic acid or gum arabic and water, to obtain granules if necessary. Then, it may be further mixed with talc or stearic acid as lubricant, and compressed into tablet by mean of common tableting machine.

Injectable formulations for parenteral route also can be prepared by dissolving the active ingredient in sterile distilled solution or sterile physiological saline solution with solution adjuvant, and filling it into ample. A stabilizer or a buffer can be used in the injectable solution. The injectable formulation may be administered intravenously or by dripping.

In administration of the flavanoids or chromones of the formula (I), the effective dosage is not particularly limited and may vary depending on the various kinds of factors, such as the target disease, the patient's condition, the severity of the disease, age, existence of a complication, as well as administration route, formulation, number of times for administration and so on. A usual recommended daily dose for oral administration is within the range of 1–1,000 mg/day/person, preferably 1–500 mg/day/person, while a usual recommended daily doses for parenteral administration is within the range of $\frac{1}{100}$ to $\frac{1}{2}$ based on dose of the oral administration. The doses also may vary depending on age, as well as the patient's condition.

The immunosuppressive agent of the present invention comprising the compound having selective inhibiting activity against activated T cells as an active ingredient, will be described in more detail in the following examples by using mice with liver injury induced by DTH reaction, and examining the apoptosis induction activity against the activated T cells isolated from these mice. However, it is to be understood that the present invention is not limited to the examples.

EXAMPLE 1

Preparation of the Rhizoma *Smilacis Glabrae* Extract (RSG ext)

Dry powdered Rhizoma *Smilacis Glabrae* was used for extraction twice with 10 times in weight of distilled water at 100° C. for 1 hour each. The combined extract was centrifuged at 1,700 g, and the resultant supernatant was lyophilized to give RSG ext in powder form in 11% yield.

The content of astilbin in the RSG ext was determined as being 0.273% by HPLC.

EXAMPLE 2

Preparation of the Extract from Rhizoma *Smilacis Glabrae*, Flavonoids and Chromones a. Extraction and Isolation 6 kg of the dried and cut Rhizoma *Smilacis Glabrae* was used for extraction with 30 L of methanol under reflux for 2 hours, and filtrated to give the extract. The residue was used for extraction with 18 L of methanol, and repeated once in the same manner as above to give the extract. Then, the residue was used for extraction again with 18 L of methanol, and repeated once in the same manner as above to give the extract. The combined extract was concentrated under reduced pressure to give 568 g of methanol extract.

This methanol extract was suspended in 1 L of water and the suspension was used for extraction three times with 1 L of petroleum ether, and successively used for extraction three times with 1 L of ethyl acetate. The combined petroleum ether extract was concentrated to give 23 g of petroleum ether extract, and also the combined ethyl acetate extract was concentrated to give 80 g of ethyl acetate extract, respectively.

70 g of ethyl acetate extract was subjected to a silica gel (1,000 g) column chromatography, and eluted with 2 L each of the mixed solution of chloroform and methanol (19:1 and 4:1) to give 32.5 g of Fraction A and 28 g of Fraction B, respectively.

25 g of the Fraction A was further subjected to a silica gel (500 g) column chromatography, and eluted with 1 L each of the mixed solution of chloroform and methanol (9:1 and 4:1) to give 2.5 g of Fraction A-1 and 7.5 g of Fraction A-2, respectively. Then, 2.0 g of the Fraction A-2 was further purified by HPLC using Cosmosil 75$C_{18}$-OPN column with methanol-water (2:3 and 3:2, each 200 ml) to give 72 mg of eucryphin of the formula (I-d).

On the other hand, 28 g of the Fraction B was further purified by HPLC using Cosmosil 75$C_{18}$-OPN column with methanol-water (3:7, 1:1 and 7:3) to give 8.2 g of astilbin of the formula (I-b) and 11.5 g of Fraction B-2, respectively. The obtained Fraction B-2 was further purified by silica gel (350 g) column chromatography with chloroform-methanol (9:1, 500 ml) and by preparative thin layer chromatography to give 2.6 g of smitilbin of formula (I-a) and 42 mg of engeletin of formula (I-c).

Table 1 below shows the amounts and yields of flavonoids and chromones from 568 g of the methanol extract, respectively.

TABLE 1

|  | Smitilbin (I-a) | Astilbin (I-b) | Engeletin (I-c) | Eucryphin (I-d) |
|---|---|---|---|---|
| Amount(g) | 2.6 | 8.2 | 0.042 | 0.072 |
| yield(%) | 0.523 | 1.650 | 0.008 | 0.071 | b. Identification of the Chemical Structure (physical data)

The chemical structures of astilbin, engeletin and eucryphin, known compounds, are identified with Mass spectrum and NMR analysis. Since smitilbin of formula (I-a) is a new compound, the chemical structure of this compound was determined by following physical data.
Appearance: colorless needle-shaped crystal (from the mixed solution of chloroform-methanol (9:1)).
Melting point: 179~181° C.
$[\alpha]^{25}_D$ -161.4° (c 0.2, MeOH).
UV (MeOH): λmax (log ε)=217 nm(4.394), 291 nm(4.279).
IR: vmax=3500(OH), 1620(C=O), 1360, 1160, 1040, 970, 820, 780 $cm^{-1}$.
HR-FAB-MS: m/z=451.1234 (calculated for $C_{21}H_{23}O_{11}$; 451.1240)
$^1$H-NMR (DMSO-$d_6$): 0.79(3H, d, J=6.0 Hz, H-6"), 2.37 (1H, m, H-5"), 3.04(1H, t, J=9.5Hz, H-4"), 3.20(1H, dd, J=9.5 & 2.9 Hz, H-3"), 3.47(1H, brs, H-2"), 4.15(1H, d, J=2.0 Hz, H-3), 4.74(1H, s, H-1"), 5.43(1H, d, J=2.0 Hz, H-2), 5.90(1H, brs, H-6), 5.92(1H, brs, H-8), 6.70(2H, brs, H-4', 6'), 6.81(1H, brs, H-2'), 11.63(1H, s, OH-5).

$^{13}$C-NMR(DMSO-$d_6$): 80.85(C-2), 74.38(C-3), 193.64 (C-4), 164.75(C-5), 101.19(C-6), 167.77(C-7), 96.20(C-8), 163.30(C-9), 97.30(C-10), 127.38(C-1'), 115.00(C-2'), 145.86(C-3'), 116.18(C-4'), 145.62(C-5'), 118.87(C-6'), 99.55(C-1"), 71.01(C-2"), 71.01(C-3"), 72.11(C-4"), 69.84 (C-5"), 18.11(C-6").

The Rf value of the acidic hydrolysis product from the compound of formula (I-a) was identified with L-rhamnose monohydrate.

The RSG ext obtained in Example 1 above, or the compound obtained in Example 2 was used in the following experiments.

EXAMPLE 3

Liver Injury Model in Mice

Experiment 1: Preparation of Mice with Liver Injury Induced by Delayed-type Hypersensitivity (DTH) Reaction, and Assay Thereof a. Methods 6–8 weeks old BALB/c mice (male and female, 22±2 g), were sensitized twice by painting 0.1 ml of 1% picryl chloride in ethanol on the skin of their abdomens at an interval of 5 days. Five days after the second sensitization, the blood samples were collected from each mice, and then mice were injected with 10 μl of 0.2% picryl chloride in olive oil into the liver for elicitation of injury. Followed by 0, 6, 12, 18 and 24 hours after elicitation, the blood samples were collected, and spleen cells, HC and NPC were isolated. The blood was used for determining the activities of alanine aminotransferase (ALT) and aspartate aminotransferase (AST).

Both spleen cells and NPC were subjected to the reaction with anti-mouse LFA-1 (lymphocyte function associated antigen-1) antibodies, and HC was subjected to the reaction with anti-mouse ICAM-1 (intercellular adhesion molecule-1) antibodies, respectively. After washing, the cells were subjected to the reaction with FITC-labeled goat anti-rat IgG. Then, the cells were washed with PBS and suspended again to determine the expression of cell surface antigen using a FACScan system (Becton Dickinson).

Furthermore, HC was co-cultured with NPC or spleen cells isolated from normal mice and liver injury mice (0, 6, 12, 18 and 24 hours after, respectively). The ALT releasing assay in supernatant was performed by following method.

HC (1×$10^5$ cells/ml) were suspended in WE medium (William's Medium E containing 2 mM L-glutamine, 10% (v/v) fetal-calf serum, 100 U/ml of penicillin and 100 μg/ml of streptomycin). Cells were seeded onto 24-well plates and pre-cultured at 37° C. with 5% (v/v) $CO_2$ in air for 5 hours. After pre-culture, HC were washed twice with WE medium, and then NPC (4×$10^5$ cells/ml) or spleen cells (5×$10^6$ cells/ml) were added to the wells. After 3 hours continuous culture, the supernatant was collected for assaying ALT activity.

b. Results

Part 1

The changes in serum ALT activity, the expression of LFA-1 on spleen cells and NPC, and the expression of ICAM-1 on HC were observed. Also, the histological changes of liver cells in liver injured mice were observed.

As the result, the expression of LFA-1 on spleen cells reached the peak at 6 hours after elicitation of liver injury. In comparison with this, the expression of LFA-1 on NPC and ICAM-1 on HC reached the peak at 12 hours after elicitation of liver injury. Serum ALT activity reached the peak after 18 hours.

With respect to the histological changes in mice, the condition of liver was almost normal at the time of inducing liver injury (0 hour). However, mild inflammatory infiltration at 6 hours after, remarked inflammatory infiltration at 12 hours after, and massive hepatocellular necrosis at 18 hours after elicitation of liver injury were observed.

Part 2

The changes of ALT-releasing activity by NPC and spleen cells against HC after elicitation of liver injury, and releasing changes of ALT in the culture supernatant of HC with NPC or spleen cells from normal and liver injured mice were observed.

As the result, the ALT releasing activity of NPC reached the peak at 12 hours after elicitation of liver injury. In the case of spleen cells, the releasing activity was maintained at the peak during 6 to 12 hours after elicitation of liver injury. The activity level of NPC at 12 hours after inducing liver injury showed approximately 12.5 times stronger than that of spleen cells at 12 hours after inducing liver injury.

From the above results, it is confirmed that the activated T cells can be prepared by inducing liver injury in mice. That is, mice were sensitized twice by painting of picryl chloride on the skin of their abdomens at an interval of 5 days, and 5 days after the sensitization, picryl chloride (i.e., same antigen) was injected into liver for elicitation of liver injury in order to prepare the activated T cells. In particular, the expression of LFA-1 on NPC and ICAM-1 on HC reached the peak at 12 hours after injecting picryl chloride into the liver, thus causing the strong immune response. Because serum ALT elevation reached the peak during such immune response, it is confirmed that the liver injury occurred due to the immune response.

Furthermore, the ALT activity in the culture supernatants of HC with NPC, isolated from mice 12 hours after injection of picryl chloride to liver, reached the peak. Accordingly, to examine the selective inhibiting activity of the activated T cells in vitro system, mice with liver injury immunologically-induced by delayed-type hypersensitivity (DTH) reaction, are preferably used.

Therefore, mice 12 hours after elicitation of liver injury by percutaneously sensitization of picryl chloride followed by further injection of the same antigen (picryl chloride) into the liver, are used in the following Examples.

EXAMPLE 4

Effect of Astilbin and RSG ext

Experiment 1 Preparation of Liver Injured Mice

Using the same manner as described in Example 3 above, 6–8 weeks old BALB/c mice (male, 22±2 g) and 6–8 weeks old ICR mice (male, 22±2 g) were sensitized twice by painting 0.1 ml of 1% picryl chloride in ethanol on the skin of their abdomens at an interval of 5 days. Five days after the second sensitization, the blood samples were collected from each mice, then the mice were injected with 10 μl of 0.2% picryl chloride in olive oil into the liver for elicitation of liver injury. 12 hours after the injection, the blood samples were collected and liver cells were isolated. The ALT and AST activities of the bloods were determined by the conventional methods. Furthermore, the liver cells were isolated from normal and liver injury mice, and HC were separated from NPC by the two-steps perfusion method. Then, these cells were used immediately for co-culture test or for apoptosis measurement.

Additionally, a part of NPC was incubated on the culture plate for 3 hours in order to separate adherent cells from non-adherent cells. The isolated HC and NPC were found to be about 90% viable as determined by trypan blue strain.

Experiment 2: Apoptosis Measurements No. 1
(Counting of Apoptotic Cells)

a. Methods

HC and NPC isolated from liver injury mice 12 hours after elicitation, and fraction of adherent cells and non-adherent cells isolated from NPC were used.

These cells were incubated with $5 \times 10^{-5}$ g/ml of astilbin and RSG ext, as the testing compounds, in RPMI 1640 medium at 37° C. for 1 hour, respectively. After incubation, the cells were stained with Hoechst 33342 (Molecular Probes, Inc., USA) for 1 minute at room temperature. After washed three times with RPMI 1640 medium, the obtained cells were fixed with 2% formaldehyde in phosphate buffer solution (PBS). The apoptotic cells among the total population were determined by counting a total of 200 cells in five different fields under fluorescent microscope.

For the control studies, the cells treated without test compounds were incubated and followed by the same manner.

b. Results

Figure 1:
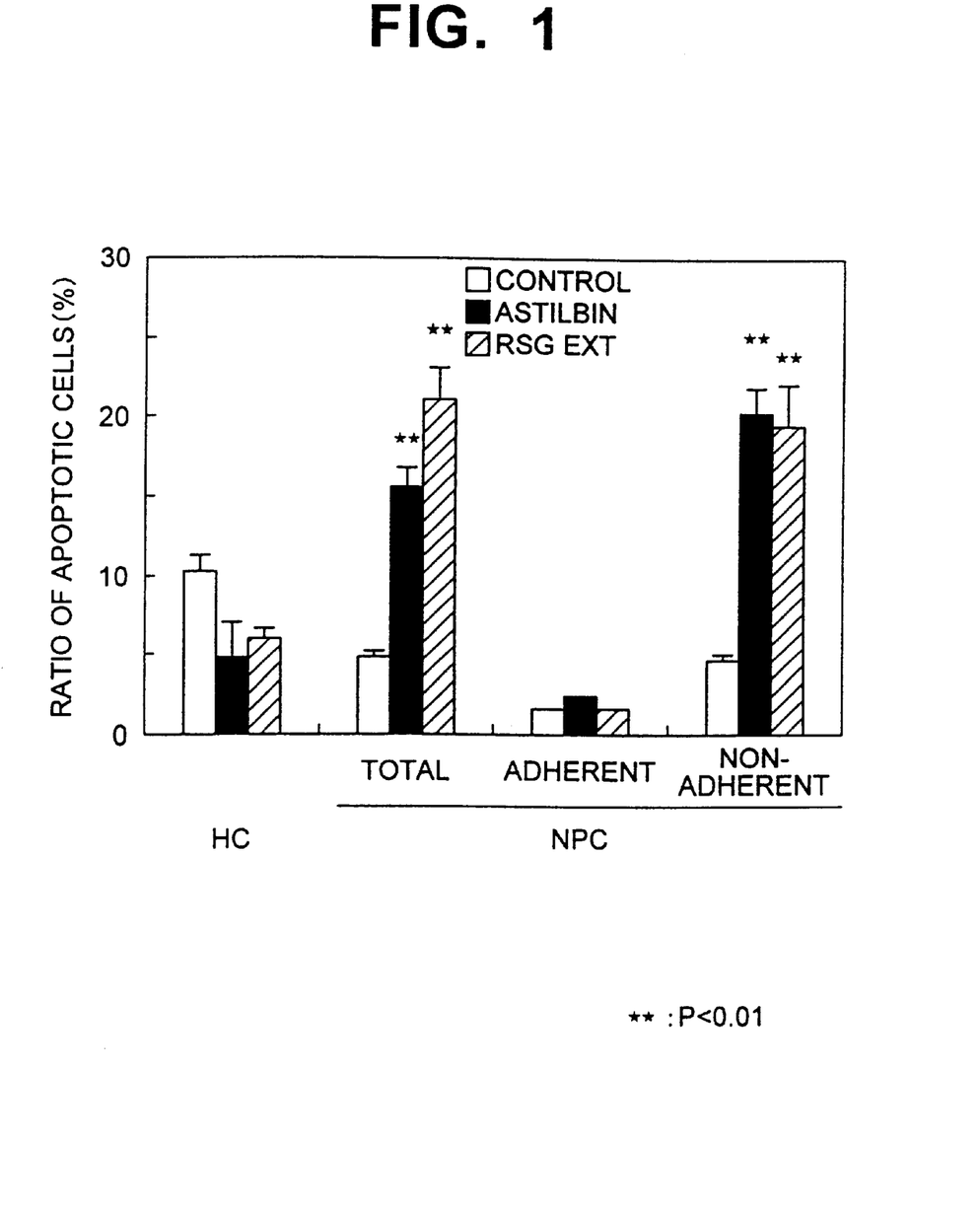
FIG. 1 shows the results of Experiment 2 of Example 4.

The effects of astilbin and RSG ext on the apoptosis of the NPC and the HC from liver injury mice were shown in FIG. 1. As indicated in FIG. 1, the ratio of apoptotic cells in total drug-untreated HC and NPC was approximately 10% and 5%, respectively. On the contrary, astilbin or RSG ext at $5 \times 10^{-5}$ g/ml significantly increased the ratio of apoptotic cells in the case of total NPC, but not in the case of HC. The ratio of apoptotic cells in non-adherent fraction isolated from NPC increased by either of the drugs, while no influence was observed in the fraction of adherent cells.

Experiment 3: Apoptosis Measurements No. 2;
DNA Fragmentation Assay (Gel agarose electrophoresis)

a. Methods

NPC isolated from normal mice and liver injury mice 12 hours after elicitation were used. These cells were treated with astilbin or RSG ext, then DNA fragmentation assay was performed by using Gel agarose electrophoresis, as follows.

The NPC isolated from normal mice and liver injury mice 12 hours after elicitation, were incubated alone, or with $5 \times 10^{-5}$ g/ml of astilbin or RSG ext, in RPMI 1640 medium at 37° C. for 1 hour. After incubation, the portions of $10^6$ cells with or without drug treatment were washed and centrifuged. The obtained precipitates were re-suspended in 0.6 ml of Lysing buffer solution (10 mM Tris, 1 mM EDTA, pH 7.5) containing 0.2% Triton X-100, and stood for 10 minutes under ice-cooling. After centrifugation at 20,000 g, the obtained supernatants were mixed with the equal volume of TE-saturated phenol and the mixture was stirred gently for 2~3 minutes, then centrifuged again. The obtained supernatants were mixed with chloroform-isoamylalcohol (24:1) solution, then the mixture was centrifuged at 20,000 g again. The obtained supernatants were stored overnight at −20° C. in 0.3 M NaCl and 70% ethanol to obtain DNA precipitates.

The DNA precipitates thus obtained were incubated with 1 μl of 1 mg/ml RNase A at 37° C. for 30 minutes. To this solution was added 1:10 (v/v) ratio of Loading buffer solution containing 0.02% bromophenol blue, 0.02% xylene cyanol FF, 50% glycerol and 0.1% SDS. Electrophoresis was carried out in 2% gel agarose for 75 minutes at 50 V, and DNA was visualized with ethidium bromide.

b. Results

In DNA fragmentation of gel agarose electrophoresis, DNA ladder' pattern appeared in the case of NPC isolated from liver injury mice, when the cells were treated with astilbin or RSG ext. On the other hand, in the case of NPC and spleen cells isolated from normal mice with these drugs, no DNA ladder' pattern appeared. Namely, apoptosis of NPC and spleen cells from normal mice was not observed.

From the results of DNA fragmentation assay, cell death of NPC isolated from liver injury mice 12 hours after elicitation by the challenge of antigen (picryl chloride), due to the treatment with astilbin, was characterized as apoptosis. These results were well identified with the results obtained in Experiment 2 above, in which no cell death of NPC from normal mice was observed by staining with Hoechst 33342.

The present inventors have already found that a great change in cell composition in NPC was found after percutaneously sensitization of picryl chloride in liver by flow cytometric analysis. The present inventors also have found that in the case of splenectomy before the challenge of antigen, the serum ALT level, which is the parameter of liver injury level, significantly lowered. Therefore, the liver infiltration and localization of lymphocytes cause a change of the composition of NPC which was suggested to be a main cause of the liver injury.

Furthermore, the results of the experiments in Example 3 clearly show that the inflammatory infiltration in histology and the hepotocellular cytotoxicity of NPC in vitro reached the peak at 12 hours after the challenge of antigen. At this stage, NPC contain 72.6~78% of LFA-1 positive cells comprising 47.9% of CD4$^+$ and 23.2% of CD8$^+$ T cells. By the treatment of such NPC with anti-CD4 monoclonal antibody plus complement, the release of ALT from HC was completely inhibited. And by the treatment of such cells with anti-CD8 antibody, the release of ALT from HC tended to be inhibited.

From these findings mentioned above and the results of the previous Example 4, it is concluded that astilbin or RSG ext induced apoptosis against non-adherent NPC but not adherent NPC. Therefore, the T lymphocyte populations, which are main components of non-adherent NPC, are supposed to be the main target of astilbin or RSG ext.

Furthermore, astilbin or RSG ext did not induce apoptosis against HC, and NPC and spleen cells isolated from normal mice. By these results, it is confirmed that the activated immune cells including mainly T cells are selectively inhibited by astilbin or RSG ext.

Experiment 4: ALT-releasing Assay (No. 1)

a. Methods

HC and NPC were isolated from mice 12 hours after elicitation of liver injury. Thus obtained HC was suspended in WE medium, and was seeded onto 96-wells microplates ($2 \times 10^4$ cells/0.2 ml/wells), and incubated at 37° C. for 5 hours with 5% (v/v) $CO_2$ in air. After incubation, the HC was washed twice with WE medium and co-cultured with NPC of $8 \times 10^4$ cells for 3 hours. NPC was pre-incubated for 1 hour at 37° C. with various concentration of astilbin or RSG ext. After co-culture, the supernatants were collected for assaying ALT and AST activities by the conventional methods.

b. Results

Figure 2:
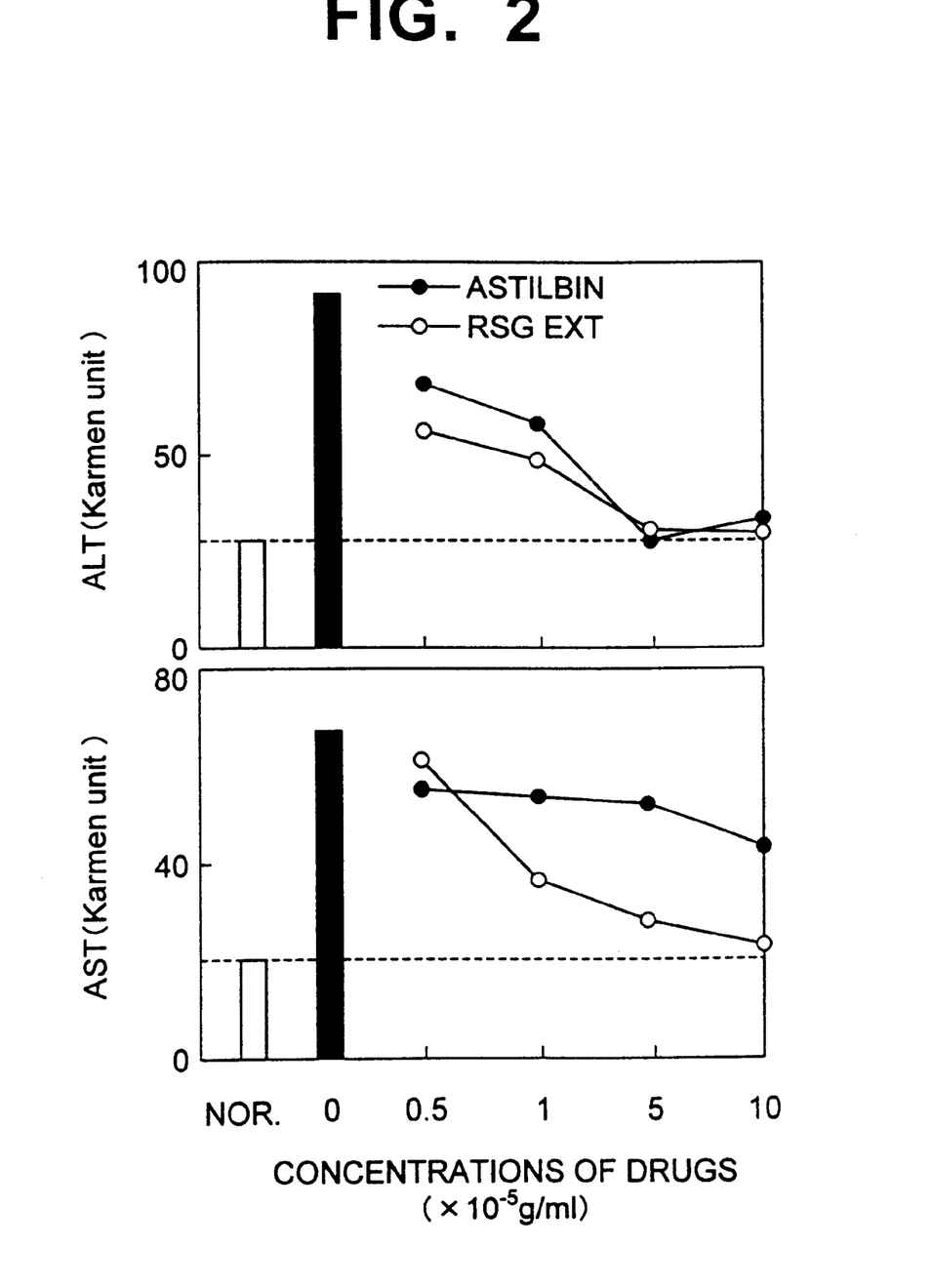
FIG. 2 shows the results of Experiment 4 of Example 4.

The results were shown in FIG. 2.

It is clear that the levels of ALT and AST from HC were significantly elevated by the co-culture with NPC for 3 hours. On the contrary, by the co-culture with NPC pre-treated with astilbin or RSG ext, the ALT releasing activity of NPC was dose-dependently inhibited, and the AST releasing activity was also dose-dependently inhibited by astilbin. $5 \times 10^{-5}$ g/ml of astilbin caused a complete inhibition of ALT release.

Experiment 5: ALT-releasing Assay (No. 2)

a. Methods

HC and NPC were isolated from liver injury mice 12 hours after elicitation, as the same manner described in Experiment 4. Thus the HC was suspended in WE medium, and was seeded onto 96-wells microplates ($2 \times 10^4$ cells/0.2 ml/wells), and incubated at 37° C. for 5 hours with 5% (v/v) $CO_2$ in air. After incubation, the HC was washed twice with WE medium and co-cultured with NPC of $8 \times 10^4$ cells, which were pre-treated with $5 \times 10^{-5}$ g/ml of astilbin or RSG ext for 5, 15, 30, 60 and 120 minutes respectively, at 37° C. for 3 hours. After co-culture, the supernatants were collected for assaying the ALT activity by the conventional methods.

b. Results

Figure 3:
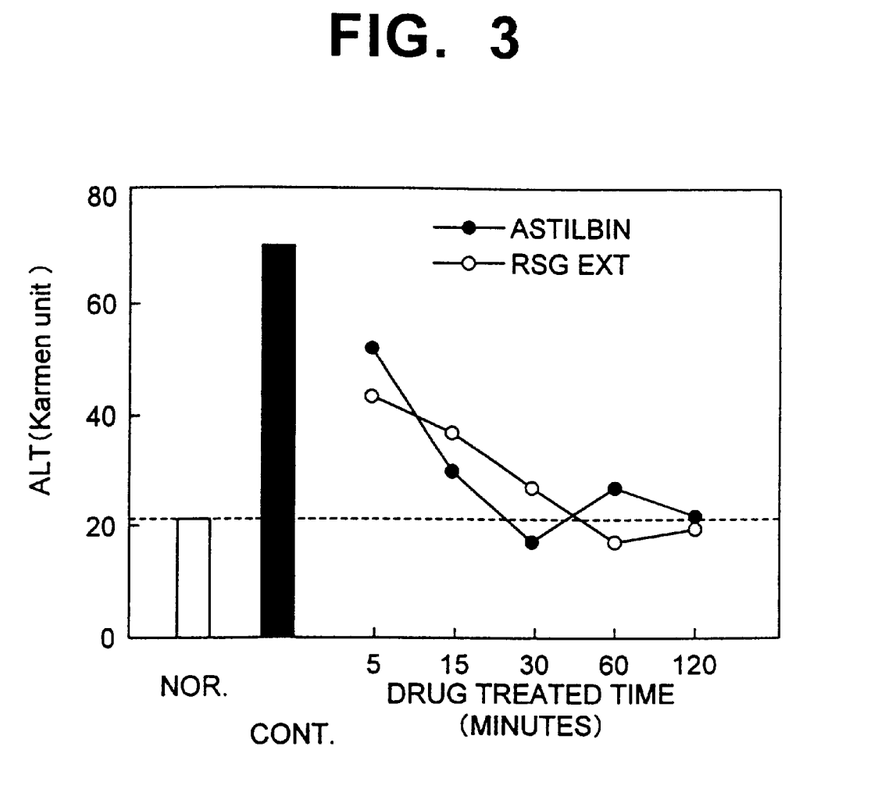
FIG. 3 shows the results of Experiment 5 of Example 4.

The results were shown in FIG. 3.

It is clear that the releasing of ALT from HC was inhibited time-dependently by the co-cultured with NPC pre-treated with astilbin or RSG ext. The ALT releasing was completely inhibited by the pre-treatment of NPC for more than 30 minutes.

When HC were pre-treated with high concentration of astilbin or RSG ext for more than 2 hours, however, the ALT releasing was not changed.

Experiment 6: ALT-releasing Activities by Oral Administration of Drugs a. Methods 6–8 weeks old BALB/c mice (male, 22±2 g) or 6–8 weeks old ICR mice (male, 22±2 g) were used. The mice were sensitized by picryl chloride on the skin by the same manner as described in Experiment 1. Then, 100 mg/kg astilbin or 200 mg/kg RSG ext were administered orally for 3 times at 0, 5 and 10 hours after the elicitation of liver injury, respectively. 2 hours after the last administration, the blood samples were collected for determining the serum ALT activity, and HC and NPC were also isolated for co-culture. The ALT activity in the supernatants was compared with the serum ALT activity.

b. Results

Figure 4:
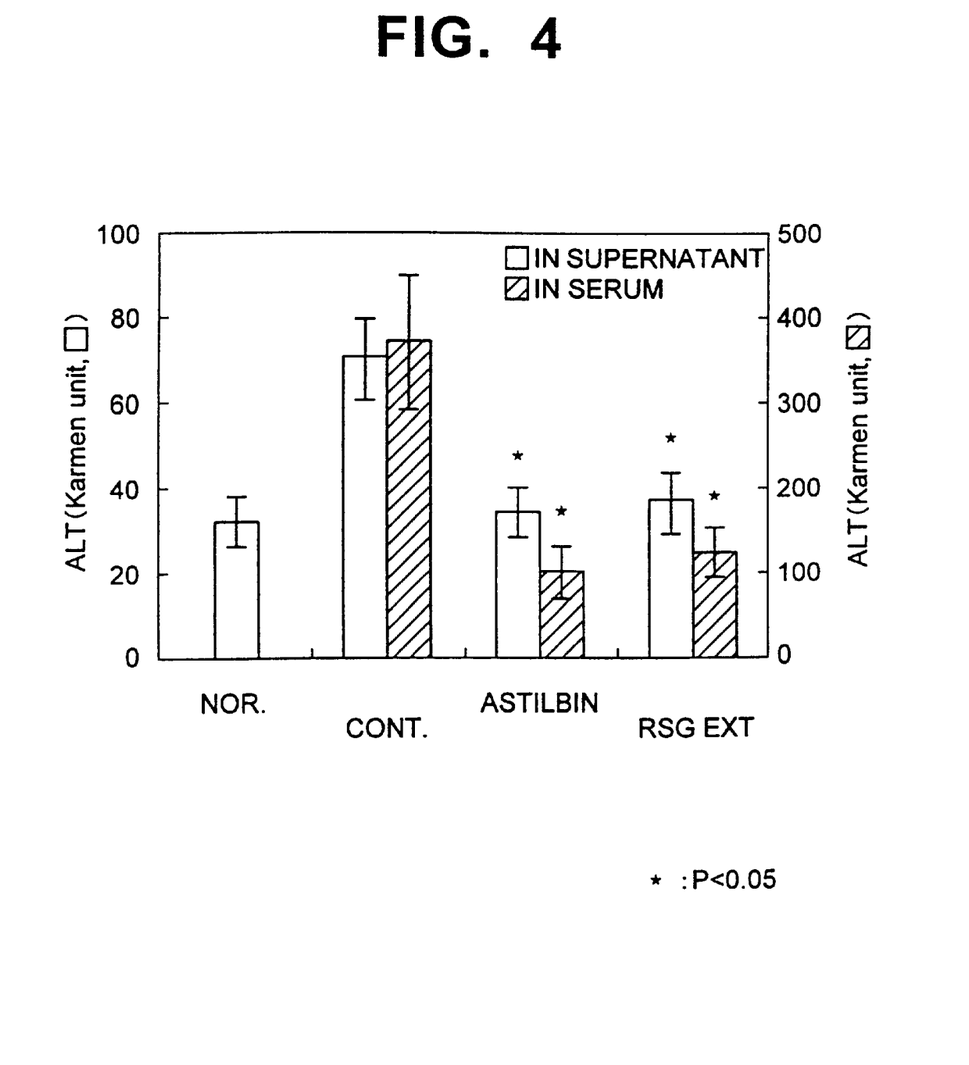
FIG. 4 shows the results of Experiment 6 of Example 4.

The results were shown in FIG. 4.

When the mice were administered the drugs orally, it is clear that the serum ALT activity and the cytotoxicity of NPC against HC was significantly decreased compared with that of the drug-untreated control mice cells.

These results were coincident with those of Experiment 4. Briefly, when NPC obtained from liver injury mice were pre-treated with astilbin or RSG ext and co-cultured with HC, the ALT activity of the supernatants obtained by co-culture was decreased compared with the drug-untreated control mice cells, and the hepatotoxic potential of NPC against HC was significantly decreased.

Experiment 7: Studies for Drug Administration Time a. Methods

The liver injury was induced by the same manner as described in Experiment 1. To determine the effects of astilbin and RSG ext on the induction phase (during sensitization) and effector phase (after elicitation of liver injury), astilbin (50 and 100 mg/kg) and RSG ext (100 and 200 mg/kg) were administered orally to the mice for once a day after 10 days from the 1st sensitization, and for 3 times at 0, 5 and 10 hours after elicitation, respectively.

For the control studies, mice without drug administration were used, and for the positive control studies, 10 mg/kg cyclophosphamide (Cy) was administered percutaneously to the mice.

Figure 5:
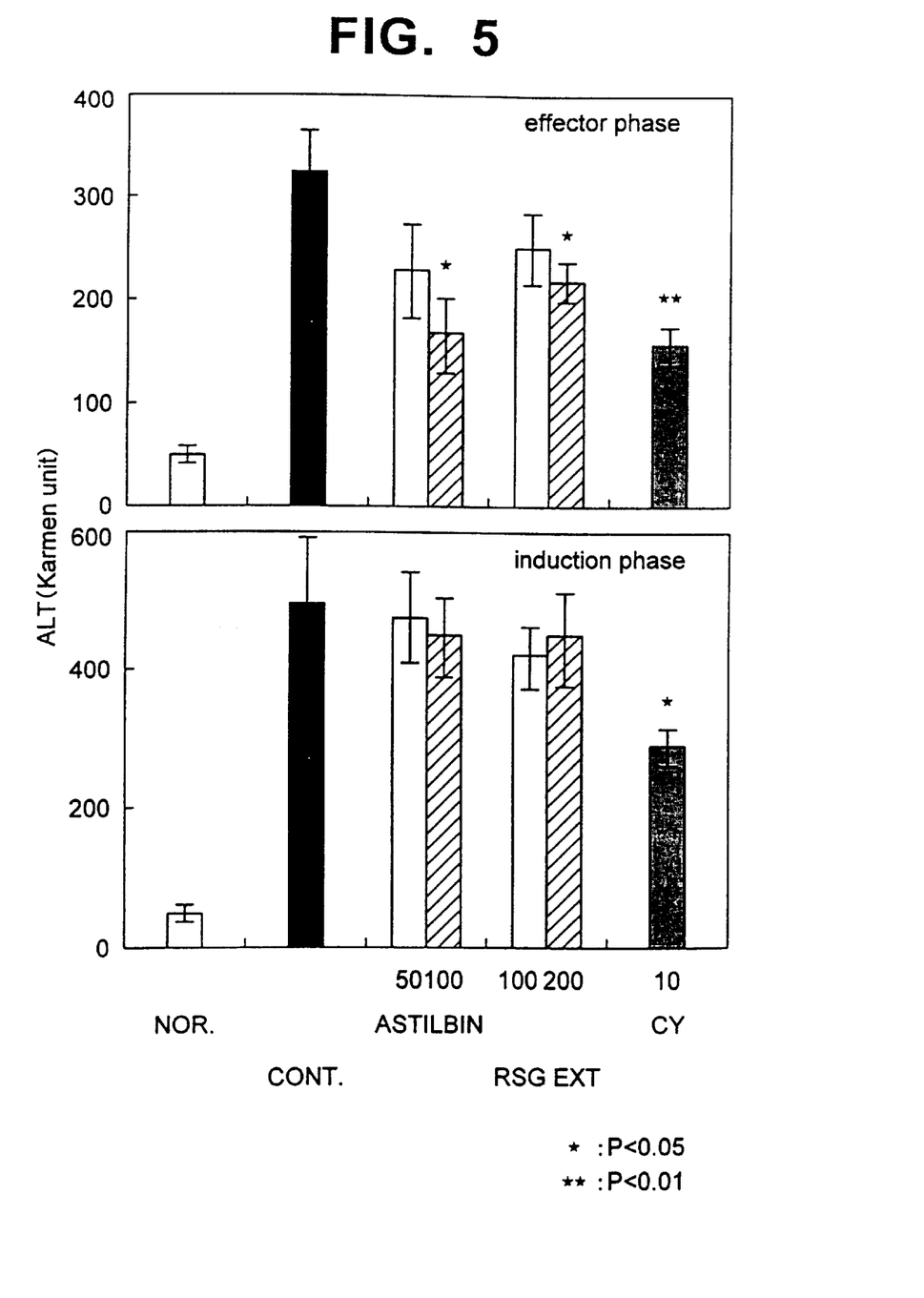
FIG. 5 shows the results of Experiment 7 of Example 4.

18 hours after the injection of picryl chloride into liver, the blood samples were collected for determining the serum ALT activity by the conventional methods. Histopathological examination of liver was also performed.

b. Results:

In FIG. 5, the effects of astilbin, RSG ext, and cyclophosphamide (Cy) on the elevation of serum ALT activity in liver injury mice were shown.

As shown in FIG. 5, a remarkable elevation in serum ALT activity was observed in the control mice in comparison to normal mice. To compare with the control mice, the mice given with high dose of both astilbin or RSG ext in effector phase mice, showed a significant decrease of the serum ALT activity and the mice given with low dose of them showed a tendency of decreasing of the serum ALT activity, and improvement of liver injury.

On the contrary, almost no improvement of liver injury was observed when the drugs were given in the induction phase. The mice administered with cyclophosphamide showed a significant decrease of the serum ALT activity, when the drugs were given in both induction and effector phases.

In histopathogical examination, the main changes in control mice were the inflammatory infiltration and hepatocellular coagulation necrosis. These changes were improved in most mice with decreasing ALT activity and improvement of liver injury by administration of astilbin, RSG ext, or cyclophosphamide was confirmed.

The foregoing results clearly demonstrate that astilbin and RSG ext show a significant inhibition of the elevation of serum ALT and AST activities when administered during the effector but not induction phase of delayed-type hypersensitivity (DTH) reaction. When NPC were pretreated with astilbin or RSG ext, a dose-dependent inhibition of ALT and AST releasing was observed, and astilbin showed a stronger activity than RSG ext.

Furthermore, these inhibitory activities of both astilbin and RSG ext were confirmed to result in a complete inhibition of ALT release and a complete dysfunction of NPC with more than 30 minutes of pre-treatment at the concentration of $5 \times 10^{-5}$ g/ml. However, when these drugs were used to treat HC before co-culture, neither astilbin nor RSG ext blocked the cytotoxicity to HC of NPC.

Therefore, it is confirmed that the improvement of liver injury is obtained by the selective eliminating the function of immune cells including mainly activated T cells.

Experiment 8: Heptoprotection Studies on $CCl_4$-induced Liver Injury in Mice a. Methods ICR male mice (8 mice for each group) were used. Astilbin (50 or 100 mg/kg) and RSG ext (100 or 200 mg/kg) were administered orally for 6 days. One hour after final administration, mice were intraperitoneally injected with 0.2% $CCl_4$ in olive oil (0.2 ml/20 g of body weight).

For the control studies, only $CCl_4$ injected mice without drug administration were used. Furthermore, for the positive control studies, 150 mg/kg of biphenyl dimethyl dicarboxylate (BDD) was administered orally to the mice.

Then, 20 hours after administration of $CCl_4$, the blood samples were collected, and used for determining the serum ALT and the serum AST activities by the conventional methods.

b. Results

Table 2 shows the test results.

TABLE 2

| Group | Dose (mg/kg) | ALT (Karmen unit) | AST (Karmen unit) |
| --- | --- | --- | --- |
| Normal | — | 244.0 ± 23.4 | 215.0 ± 23.2 |
| Control | — | 947.5 ± 27.5 | 669.4 ± 45.4 |
| Astilbin | 50 | 901.6 ± 36.1 | 670.4 ± 21.2 |
|  | 100 | 921.5 ± 40.2 | 688.2 ± 45.6 |
| RSG ext | 100 | 920.7 ± 69.2 | 662.9 ± 37.1 |
|  | 200 | 899.3 ± 37.1 | 638.1 ± 48.2 |
| BDD | 150 | 510.7 ± 27.0* | 675.6 ± 80.9 |

*p < 0.01

Table 2 clearly shows that the remarkable elevation of ALT and AST activities was observed in the control group ($CCl_4$ administered group). However, no effect was observed in either astilbin or RSG ext treated group. BDD significantly decreased the ALT elevation.

Experiment 9: Heptoprotection Studies on $CCl_4$-induced Liver Hepatocyte Damage a. Methods HC was isolated from the normal mice used in Experiment 8 above. The cells were treated for 2 hours with astilbin or RSG ext, then washed twice with WE medium solution. After washing, 0.1 ml of 0.2% $CCl_4$ in olive oil was added to the cells, and the resulting cells were incubated for 1 hour. The ALT activity in the supernatants was determined by the conventional methods.

b. Results

Astilbin and RSG ext did not affect the ALT release from HC treated with $CCl_4$ at the concentration of $5 \times 10^{-6}$ to $1 \times 10^{-4}$ g/ml.

These results show that when the drugs were used to treat HC before administration of $CCl_4$, neither astilbin nor RSG ext blocked the cytotoxicity of $CCl_4$ against HC. Furthermore, a 6-day preventive administration of both drugs failed to improve the $CCl_4$-induced liver injury in mice. Therefore, these results suggest that astilbin and RSG ext improve liver injury through selectively inhibiting the function of immune cells including mainly activated T cells rather than through the protection of HC.

EXAMPLE 5

Effect of Flavanoids and Chromones

Experiment 1: Preparation of Liver Injury in Mice by Using Picryl Chloride:

6–8 weeks old BALB/c male mice were used. Using the same manner as described in Experiment 1 of Example 4, mice were sensitized twice by painting 0.1 ml of 0.1% picryl chloride in ethanol on the skin of their abdomens at an interval of 5 days. Five days after the second sensitization, mice were injected with 10 μl of 0.2% picryl chloride in olive oil into the liver. 12 hours after the injection, HC and NPC were isolated by the modified two-step perfusion method. The obtained cells were found to be about 90% viable by trypan blue dye exclusion test, and used for the following studies.

Experiment 2: Cell Culture and ALT Releasing Assay (pre-treatment of NPC)

a. Methods

HC ($2 \times 10^4$ cells/0.2 ml/wells in WE medium) were seeded onto 96-well microplates and incubated at 37° C. with 5% (v/v) $CO_2$ in air.

On the other hand, NPC was incubated in the medium with or without test compounds for 1 hour. The test compounds were smitilbin of the formula (I-a), astilbin of the formula (I-b), engeletin of the formula (I-c), and eucryphin of formula (I-d), respectively.

After 5 hours of the incubation, each monolayers of HC were washed twice with the medium, and then $8 \times 10^4$ cells of NPC, pre-treated with or without above test compounds, were added. After 3 hours of further incubation, the supernatants were collected and used for assaying the ALT activity by the conventional methods.

b. Results

Figure 6:
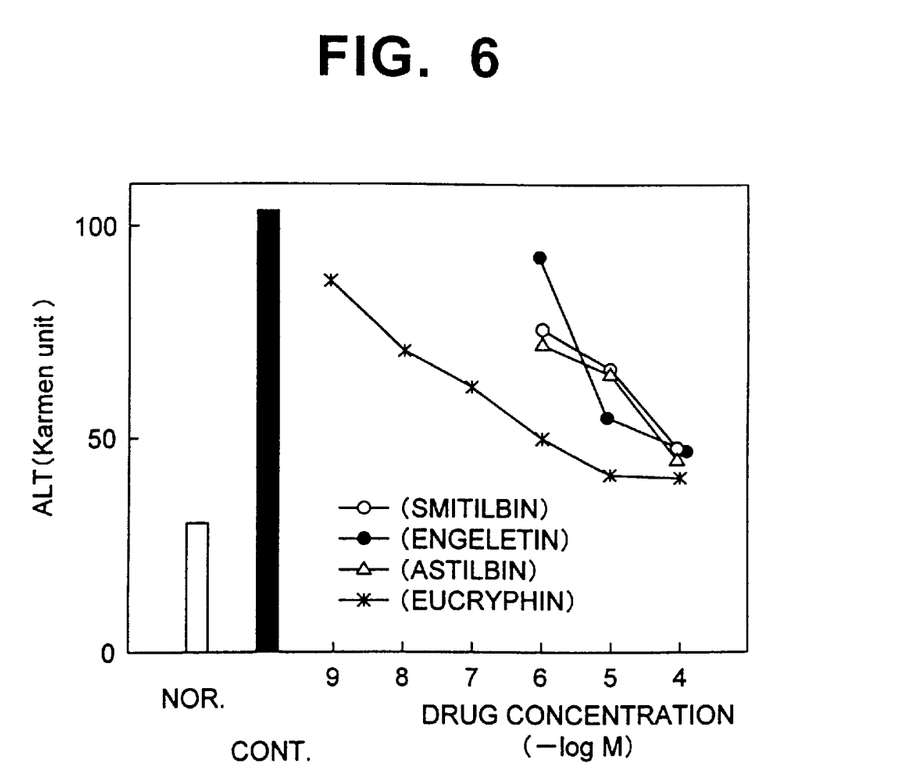
FIG. 6 shows the results of Experiment 2 of Example 5.

The results were shown in FIG. 6.

As shown in FIG. 6, a remarkable elevation of the ALT activity was observed in the supernatants of co-cultured HC with compound non-treated NPC (control). On the other hand, astilbin, smitilbin and engeltin, flavaniods having a similar structure, dose-dependently inhibited the ALT activities with a similar intensity of inhibition. Eucryphin, which is a chromone, showed a much stronger inhibitory effect.

These results suggest that the flavanoids or chromones of the present invention inhibited the cytotoxicity to HC of liver-infiltrated NPC, that is, mainly activated T cells, by the suppression of their immune function.

Experiment 3: Cell Culture and ALT Releasing Assay (pre-treatment of HC)

a. Methods

HC in WE medium was incubated with or without test compounds for 1 hour. Then, the HC was seeded onto 96-well microplates ($2 \times 10^4$ cells/0.2 ml/wells) and incubated at 37° C. with 5% (v/v) $CO_2$ in air for 5 hours. After 5 hours, HC monolayers were washed twice with the medium, and then $8 \times 10^4$ cells of NPC were added. After 3 hours of continuous incubation, the supernatants were collected for assaying of the ALT activity by the conventional methods. The test compounds were the same ones as described in Experiment 2, above.

b. Results

The ALT release induced by NPC was not influenced by all test compounds when they were used for pre-treating HC.

Experiment 4: Cell Culture and ALT Releasing Assay (influence on $CCl_4$)

a. Methods

HC isolated from the normal mice was used. The cells were treated for 2 hours with test compounds. After treatment, the cells were washed twice, and incubated for 1 hour after addition of 0.1 ml of 0.2% $CCl_4$. The obtained supernatants were collected for assaying the ALT activity by the conventional methods. For the control studies, non-treated HC with test compounds were used.

The test compounds were same ones as described in Experiment 2.

b. Results

None of the test compounds, smitilbin, astilbin, engeletin and eucryphin, suppressed the ALT release from HC injured with $CCl_4$ at the concentration of $5 \times 10^{-6}$ to $1 \times 10^{-4}$ g/ml. Therefore, the results suggest that these compounds do not have such hepatoprotective action as the stabilization of hepatocyte membranes as seen in hepatoprotective agents so far. It is suggested that the hepatoprotective action of these compounds is to suppress the immune function of the activated T cells selectively.

What is claimed is:

1. A method for treating diseases due to abnormal immune response induced by activated T cells comprising administering an effective amount of an immunosuppressive agent having a selective inhibitory activity against activated T cells, wherein said agent comprises flavanoids or chromones represented by the following formula (I):

(I)

wherein,

R is a hydrogen atom or a phenyl group which may be substituted with one or two hydroxy groups, Rha is an O-L-rhamnose residue, and the dotted line indicates with or without a double bond, as an active ingredient.

2. The method as claimed in claim 1, wherein said disease due to abnormal immune response is autoimmune disease.

3. The method as claimed in claim 2, wherein said autoimmune disease is autoimmune hepatitis, rheumatoid arthritis, insulin-dependent diabetes mellitus (IDDM), ulcerative colitis, multiple sclerosis (MS), scleroderma, myasthenia gravis, multiple myositis/dermatomyositis, Hashimoto's disease, autoimmune hypocytosis, Sjögren's syndrome, angitis syndrome or systemic lupus erythematosus.

4. The method as claimed in claim 1, wherein R of the formula (I) is a hydrogen atom, a 4-hydroxy-phenyl, a 3,4-dihydroxyphenyl, or a 3,5- dihydroxyphenl group.

5. The method as claimed in claim 1, wherein said flavanoids or chromones of the formula (I) are smitilbin of the formula (I-a), astilbin of the formula (I-b), engeletin of the formula (I-c), or eucryphin of the formula (I-d), represented by following formula (I-a)

(I-b)

(I-c)

(I-d)

6. The method as claimed in claim 1, wherein said agent comprises a plant extract containing flavanoids or chromones of the formula (I) as an active ingredient.

7. The method as claimed in claim 6, wherein said plant extract is Rhizoma Smilacis Glabrae extract.

* * * * *

UNITED STATES PATENT AND TRADEMARK OFFICE
CERTIFICATE OF CORRECTION

PATENT NO. : 6,531,505 B2
DATED : March 11, 2003
INVENTOR(S) : Qiang Xu et al.

It is certified that error appears in the above-identified patent and that said Letters Patent is hereby corrected as shown below:

Column 16,
Lines 6-35, claim 1 should read as follows:

1. A method for treating diseases due to abnormal immune response induced by activated T cells comprising administering an effective amount of an immunosuppressive agent having a selective inhibitory activity against activated T cells, wherein said agent comprises flavanoids or chromones represented by the following formula (I):

wherein,

R is a hydrogen atom or a phenyl group which may be substituted with one or two hydroxy groups, Rha is an α-L-rhamnose residue, and the dotted line indicates with or without a double bond, as an active ingredient.

Signed and Sealed this

First Day of November, 2005

JON W. DUDAS
*Director of the United States Patent and Trademark Office*